(12) United States Patent
McConnell et al.

(10) Patent No.: US 12,233,079 B2
(45) Date of Patent: Feb. 25, 2025

(54) COMPOSITION AND METHOD FOR TREATING HUMANS USING LOW-FODMAP DIETS

(71) Applicant: Glycom A/S, Hørsholm (DK)

(72) Inventors: Bruce McConnell, La Tour de Peilz (CH); Louise Kristine Vigsnæs, Copenhagen NV (DK)

(73) Assignee: Glycom A/S, Hørsholm (DK)

( * ) Notice: Subject to any disclaimer, the term of this patent is extended or adjusted under 35 U.S.C. 154(b) by 774 days.

(21) Appl. No.: 17/417,029

(22) PCT Filed: Dec. 19, 2019

(86) PCT No.: PCT/IB2019/061096
§ 371 (c)(1),
(2) Date: Jun. 21, 2021

(87) PCT Pub. No.: WO2020/128947
PCT Pub. Date: Jun. 25, 2020

(65) Prior Publication Data
US 2022/0072017 A1    Mar. 10, 2022

(30) Foreign Application Priority Data
Dec. 19, 2018 (DK) .............................. PA201801022

(51) Int. Cl.
A61K 31/702    (2006.01)
A61K 9/00      (2006.01)
A61K 9/16      (2006.01)
A61K 9/48      (2006.01)
A61K 35/20     (2006.01)
A61K 47/24     (2006.01)
A61K 47/38     (2006.01)
A61K 47/42     (2017.01)
A61K 47/44     (2017.01)
A61P 1/14      (2006.01)

(52) U.S. Cl.
CPC .......... A61K 31/702 (2013.01); A61K 9/0095 (2013.01); A61K 9/1611 (2013.01); A61K 9/1688 (2013.01); A61K 9/4825 (2013.01); A61K 35/20 (2013.01); A61K 47/24 (2013.01); A61K 47/38 (2013.01); A61K 47/42 (2013.01); A61K 47/44 (2013.01); A61P 1/14 (2018.01)

(58) Field of Classification Search
CPC .. A61K 31/702; A61K 9/0095; A61K 9/1611; A61K 9/1688; A61K 9/4825; A61K 35/20; A61K 47/24; A61K 47/38; A61K 47/42; A61K 47/44; A61P 1/14
USPC .......................................................... 514/61
See application file for complete search history.

(56) References Cited

U.S. PATENT DOCUMENTS

2012/0171166 A1   7/2012  Chow et al.
2016/0243138 A1*  8/2016  Hennet .............. A61K 31/7004
2017/0258820 A1   9/2017  Hennet et al.

FOREIGN PATENT DOCUMENTS

| AU | 2017101183 A4 | 10/2017 |
| CA | 2846603 A1 | 3/2013 |
| CN | 107073021 A | 8/2017 |
| CN | 110123822 A | 8/2019 |
| EP | 3335576 A1 | 6/2018 |
| JP | 2017533915 A | 11/2017 |
| WO | 0104341 A1 | 1/2001 |
| WO | 2007101862 A1 | 9/2007 |
| WO | 2010100979 A1 | 9/2010 |
| WO | 2010115934 A1 | 10/2010 |
| WO | 2010115935 A1 | 10/2010 |
| WO | 2011100979 A1 | 8/2011 |
| WO | 2011100980 A1 | 8/2011 |
| WO | 2012007588 A1 | 1/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013016111 A1 | 1/2013 |
| WO | 2013032674 A1 | 3/2013 |
| WO | 2013044928 A1 | 4/2013 |
| WO | 2013091660 A1 | 6/2013 |
| WO | 2013139344 A1 | 9/2013 |
| WO | 2014020004 A1 | 2/2014 |
| WO | 2016066174 A1 | 5/2016 |
| WO | 2016066175 A1 | 5/2016 |
| WO | 2017046711 A1 | 3/2017 |
| WO | 2017071716 A1 | 5/2017 |
| WO | 2017084673 A1 | 5/2017 |
| WO | 2017114733 A1 | 7/2017 |

(Continued)

OTHER PUBLICATIONS

EP19897943, "Supplementary European Search Report", European Patent Office, Jul. 28, 2022, pp. 1-2.
Perdijk et al., "Sialyllactose and Galactooligosaccharides Promote Epithelial Barrier Functioning and Distinctly Modulate Microbiota Composition and Short Chain Fatty Acid Production In Vitro", Frontiers in Immunology, vol. 10, Feb. 12, 2019, pp. 1-14.
Tsukahara et al., "G protein-coupled receptor 35 contributes to mucosal repair in mice via migration of colonic epithelial cells", Pharmacological Research, Elsevier, Jun. 23, 2017, pp. 1-13.

(Continued)

Primary Examiner — Yin-Horng Shiao
(74) Attorney, Agent, or Firm — Kunzler Bean & Adamson; Thomas D. Briscoe

(57) ABSTRACT

A synthetic composition and method for use in providing a source of oligosaccharides to a human consuming a low-FODMAP diet, increasing the abundance of bifidobacteria in the colon of a human consuming a low-FODMAP diet, and/or reintroducing FODMAPs into the diet of a human consuming a low-FODMAP diet. The composition contains one or more human milk oligosaccharides.

13 Claims, No Drawings

(56) References Cited

FOREIGN PATENT DOCUMENTS

| WO | 2017190754 A1 | | 11/2017 |
|---|---|---|---|
| WO | WO 2018/106845 | * | 6/2018 |
| WO | 2019106620 A1 | | 6/2019 |
| WO | 2019121929 A1 | | 6/2019 |
| WO | 2019122178 A1 | | 6/2019 |
| WO | 2019122190 A1 | | 6/2019 |
| WO | 2019123316 A1 | | 6/2019 |

OTHER PUBLICATIONS

Longstreth et al., Functional Bowel Disorders, Gastroenterology, 2006, p. 1480-1491, vol. 130.
Simren et al., New treatments and therapeutic targets for IBS and other functional bowel disorders, Nature Reviews Gastroenterology & Hepatology, Jun. 21, 2018, p. 589-605, vol. 15.
Kim et al., Methanobrevibacter smithii is the Predominant Methanogen in Patients with Constipation-Predominant IBS and Methane on Breath, Digestive Diseases and Sciences, May 10, 2012, p. 3213-3218, vol. 57.
Duranti et al., Exploration of the Genomic Diversity and Core Genome of the Bifidobacterium adolescentis Phylogenetic Group by Means of a Polyphasic Approach, Applied and Environmental Microbiology, Dec. 19, 2013, p. 336, vol. 79 No. 1.
Bottacini et al., Diversity, ecology and intestinal function of bifidobacteria, Microbial Cell Factories, Aug. 29, 2014, vol. 13 No. S4.
Commission Notice on the classification of Food for Special Medical Purposes, Official Journal of the European Union, Nov. 25, 2017, p. 10-11.
Urashima et al., Milk Oligosaccharides, Nutrition and Diet Research Progress, 2011, Nova Science Publishers, Inc.
Chen, Xi, Chapter Four—Human Milk Oligosaccharides (HMOS): Structure, Function, and Enzyme-Catalyzed Synthesis, Advances in Carbohydrate Chemistry and Biochemistry, 2015, p. 113-190, vol. 72.
Klindworth et al., Evaluation of general 16S ribosomal RNA gene PCR primers for classical and next-generation sequencing-based diversity studies, Nucleic Acids Research, Jan. 1, 2013, p. e1, vol. 41 Issue 1.
Staudacher et al., Altered gastrointestinal microbiota in irritable bowel syndrome and its modification by diet: probiotics, prebiotics and the low FODMAP diet, Proceedings of the Nutrition Society, Feb. 24, 2016, p. 312-315, vol. 75, Issue 3.
PCT/IB2019/061096, "Notificataion of Transmittal of the International Search Report and the Written Opinion of the International Searching Authority, or the Declaration", Mar. 17, 2020, pp. 1-20.
T. Tsukahara et al., "G protein-coupled receptor 35 contributes to mucosal repair in mice via migration of colonic epithelial cells" Pharmacological Research 123, Jun. 23, 2017, pp. 27-39.
A.C. Ford et al., "Glucocorticosteroid Therapy in Inflammatory Bowel Disease: Systematic Review and Meta-Analysis", The American Journal of Gastroenterology, vol. 106, Apr. 2011, pp. 590-599.
H.D. Holscher et al., "Human Milk Oligosaccharides Influence Maturation of Human Intestinal Caco-2Bbe and HT-29 Cell Lines", The Journal of Nutrition, Nutrient Physiology, Metabolism, and Nutrient-Nutrient Interactions, Feb. 5, 2014, pp. 586-591.
M.F. Neurath et al., "Mucosal healing in inflammatory bowel diseases: a systematic review", Downloaded from http://gut.bmj.com/ on Oct. 25, 2016—Published by group.bmj.com, pp. 1619-1635.
K.F. Frøslie et al., "Mucosal Healing in Inflammatory Bowel Disease: Results From a Norwegian Population-Based Cohort", Gastroenterology, Aug. 2007, pp. 412-422.
O. Perdijk et al, "Sialyllactose and Galactooligosaccharides PromoteEpithelial Barrier Functioning and Distinctly Modulate Microbiota Composition and Short Chain Fatty Acid Production In Vitro", Frontiers in Immunology, Feb. 12, 2019, pp. 1-14.
P.R. Gibson et al., "History of the low FODMAP diet", Journal of Gastroenterology and Hepatology, Nov. 29, 2016, pp. 5-7.
G.R. Gibson et al., "The International Scientific Association for Probiotics and Prebiotics (ISAPP) consensus statement on the definition and scope of prebiotics", Nature Reviews, Gastroenterology & Hepatology, vol. 14, Aug. 2017, pp. 491-502.
I.K. Wiklund et al., "An Irritable Bowel Syndrome-Specific Symptom Questionnaire: Development and Validation", Scandinavian Journal of Gastroenterology, Jul. 8, 2009, pp. 1-9.
B. Ljotsson et al., "Discriminant and convergent validity of the GSRS-IBS symptom severity measure for irritable bowel syndrome: A population study", United European Gastroenterology Journal, vol. 8, (2020), pp. 284-292.
J. Varney, Lactose Breath Resting—Is it really useful?, https://www.monashfodmap.com/blog/lactose-breath-testing-it-really-useful, Monash University, Jan. 5, 2018, pp. 1-2.
M. Di Costanzo et al., "Lactose Intolerance: Common Misunderstandings", Annals or Nutrition & Metabolism, Feb. 19, 2019, pp. 30-37.
E. Elison et al., "Oral supplementation of healthy adults with 2'-O-fucosyllactose and lacto-N-neotetraose is well tolerated and shifts the intestinal microbiota", British Journal of Nutrition, Oct. 10, 2016, pp. 1356-1368.

\* cited by examiner

COMPOSITION AND METHOD FOR TREATING HUMANS USING LOW-FODMAP DIETS

CROSS-REFERENCE TO RELATED APPLICATIONS

This application is a National Stage Entry under 35 U.S.C. § 371 of International Application PCT/IB2019/061096 filed on Dec. 19, 2019, which claims priority to Danish Patent Application No. PA 2018 01022 filed Dec. 19, 2018, the entirety of each of which are incorporated herein by reference.

FIELD OF THE INVENTION

This invention relates generally to compositions and methods for the management and/or treatment of humans using low-FODMAP diets, in particular irritable bowel syndrome patients using low-FODMAP diets to manage symptoms.

BACKGROUND TO THE INVENTION

Irritable bowel syndrome is a clinically heterogeneous disorder involving chronic symptoms such as abdominal pain, abdominal discomfort, abdominal bloating, fatigue, and changes in bowel movement patterns, such as patterns of loose or more frequent bowel movements, diarrhoea and constipation. Routine clinical tests on patients typically show no abnormalities, although their bowels may be more sensitive to certain stimuli, such as balloon insufflation testing. The worldwide prevalence of IBS is about 10-20% (Longstreth et al. *Gastroenterology* 130, 1480 (2006)) but may be higher in certain countries. The causes of IBS are unknown but the current view of the pathophysiology of IBS is that it is a disorder of disturbed gut-brain interactions, with relevant abnormalities at different sites along the gut-brain axis, including altered gastrointestinal motility, visceral hypersensitivity, increased intestinal permeability, immune activation and altered gut microbiota (Simrén et al. *Nat. Rev. Gastroenterol. Hepatol.* 15, 589 (2018)). Factors potentially causing IBS include acute gastrointestinal infections, small intestinal bacterial overgrowth, antibiotic usage and dysbiosis are thought to be important risk factors (Kim et al. *Digest. Dis. Sci.* 57, 3213 (2012)). Other risk factors are young age, prolonged fever, anxiety, and depression. Chronic low-grade inflammation commonly occurs in IBS patients, but there are otherwise little or no observable clinical manifestations.

Diagnosis of IBS is difficult. No biomarker-based tests can be performed to diagnose IBS. Diagnosis generally involves excluding conditions that produce IBS-like symptoms and then following a procedure to categorise a patient's symptoms. Ruling out parasitic infections, lactose intolerance, and celiac disease is recommended for all patients before a diagnosis of IBS is made. Once diagnosed, patients are usually classified in accordance with the Rome IV criteria into three main subtypes based on abdominal bowel movements: diarrhoea predominant (IBS-D), constipation predominant (IBS-C), and mixed subtype (IBS-M) with alternating episodes of both diarrhoea and constipation. Patients who meet the diagnostic criteria for IBS but who do not fall into the 3 main subtypes are then considered as IBS unclassified (IBS-U).

There is no cure for IBS and currently, effective treatment options are limited. Most of treatment options target individual symptoms and not the overall disease burden. This approach is partly related to incomplete understanding of the underlying pathophysiology of IBS. The current first-line therapies for IBS target the predominant symptom and mainly affect one symptom in the symptom complex. For patients with IBS-D, the μ-opioid receptor agonist Loperamide is recommended, although the available evidence of efficacy is limited. For patients with IBS-C, increasing the intake of dietary fibre is often recommended, particularly soluble fibre, for example, psyllium and ispaghula husk. This recommendation is associated with a beneficial effect on constipation, but effects on other IBS symptoms are less prominent. Osmotic laxatives, such as polyethylene glycol (PEG), are also used. For patients with IBS who have pain predominance, antispasmodics are often used as first-line treatments. These drugs mainly involve anticholinergic actions or calcium antagonism, leading to smooth muscle relaxation in the gastrointestinal tract and hence reduction of pain.

Most patients with IBS report worsening of symptoms after food ingestion. For example, foods rich in incompletely absorbed carbohydrates, fatty foods and high-caloric meals often cause issues. Dietary advice recommendations usually take the form of 'healthy eating' advice. The current recommendation is to modify intake of alcohol, caffeine, fat, spicy foods and gas-producing foods, to focus on meal size and number of meals per day and to assess the possibility of food intolerances, especially milk or lactose. Further, dietary fibre intake might be reduced if bloating is a predominant feature.

These approaches are usually not fully satisfactory and do not lead to adequate symptom control. For this reason, many patients adopt a diet which is low in fermentable oligosaccharides, disaccharides, monosaccharides and polyols (FODMAPs). These carbohydrates can be incompletely absorbed in the small intestine and pass into the large intestine where they are fermented by intestinal bacteria, leading to gas production and bloating. Also, they may stimulate motility by causing a net flux of water into the lumen. Results from several clinical trials suggest that some patients with IBS have a favourable, short-term response to a low-FODMAP diet. However, even short-term use of the low-FODMAP diet has been associated with potentially unfavourable changes in intestinal microbiota composition. Also, the diet is difficult to comply with over the long term and proper application requires the gradual reintroduction of some sources of FODMAPs because many of these sources (e.g. fruits and vegetables) are important for healthy nutrition. Upon reintroduction of FODMAPs, the symptoms often return. Patients are therefore left with the choice of remaining on a difficult diet which is potentially unhealthy over the long term, or reintroducing foods which may trigger symptoms.

WO 2016/066175 discloses compositions containing one or more human milk oligosaccharides (HMOs) for treating IBS in patients suffering from bacterial overgrowth, intestinal dysbiosis and gut barrier dysfunction. EP-A-2451462 discloses compositions for treating inflammatory bowel disease or irritable bowel syndrome containing one or more HMOs. The HMOs are stated to inhibit inflammation. Neither document addresses issues associated with low-FODMAP diets.

Therefore, there remains a need for approaches to address nutritional deficiencies and intestinal dysbiosis in patients consuming a low-FODMAP diet without inducing substantial gastrointestinal symptoms. Also, there remains a need for approaches to reduce or prevent symptoms in patients who are consuming a low-FODMAP diet but wish to reintroduce sources of FODMAPs into their diet.

SUMMARY OF THE INVENTION

In one aspect, this invention provides one or more human milk oligosaccharides for use in:
1. providing a source of oligosaccharides to a human consuming a low-FODMAP diet without inducing gastrointestinal symptoms in the human;
2. increasing the abundance of bifidobacteria in the colon of a human consuming a low-FODMAP diet;
3. permitting reintroduction of FODMAPs into the diet of a human consuming a low-FODMAP diet without inducing gastrointestinal symptoms in the human; and/or
4. prolonging gastrointestinal symptom reduction in a human tapering off or terminating a low-FODMAP diet.

A second aspect of the invention relates to a synthetic composition for use in:
1. providing a source of oligosaccharides to a human consuming a low-FODMAP diet without inducing gastrointestinal symptoms in the human;
2. increasing the abundance of bifidobacteria in the colon of a human consuming a low-FODMAP diet;
3. permitting reintroduction of FODMAPs into the diet of a human consuming a low-FODMAP diet without inducing gastrointestinal symptoms in the human; and/or
4. prolonging gastrointestinal symptom reduction in a human tapering off or terminating a low-FODMAP diet, the composition comprising an effective amount of one or more human milk oligosaccharides.

The synthetic composition can comprise a source of protein, a source of lipids, and a source of carbohydrate which is low in FODMAPs.

The amount of the one or more human milk oligosaccharides is preferably effective to increase the abundance and/or relative abundance of bifidobacteria and/or butyrate-producing bacteria in the colon of the human. Further, the amount of the one or more human milk oligosaccharides is preferably effective to improve the intestinal barrier properties of the human, particularly in the colon. Preferably, the synthetic composition contains an amount of 0.5 g to 15 g of the one or more human milk oligosaccharides, more preferably 1 g to 10 g. For example, the synthetic composition may contain 2 g to 7.5 g of the one or more human milk oligosaccharides.

The synthetic composition may contain a bifidobacteria, for example, *Bifidobacterium longum*, *Bifidobacterium infantis* and/or *Bifidobacterium bifidum*.

A third aspect of the invention is a pack for use in:
1. providing a source of oligosaccharides to a human consuming a low-FODMAP diet without inducing gastrointestinal symptoms in the human;
2. increasing the abundance of bifidobacteria in the colon of a human consuming a low-FODMAP diet; and/or
3. permitting reintroduction of FODMAPs into the diet of a human consuming a low-FODMAP diet without inducing gastrointestinal symptoms in the human; and/or
4. prolonging gastrointestinal symptom reduction in a human tapering off or terminating a low-FODMAP diet, the pack comprising at least 14 individual daily doses of an effective amount of one or more human milk oligosaccharides.

The individual daily doses in the pack preferably contain an amount of 0.5 g to 15 g of the one or more human milk oligosaccharides, more preferably 1 g to 10 g. For example, the pack may contain 2 g to 7.5 g of the one or more human milk oligosaccharides. Further the pack preferably comprises at least about 21 individual daily doses, for example, about 28 daily doses.

A fourth aspect of the invention is a use of
a human milk oligosaccharide (HMO),
a synthetic composition comprising an HMO, or
a pack comprising at least 14 individual daily doses of an effective amount of one or more HMOs
in the dietary management of a human consuming a low-FODMAP diet.

A fifth aspect of the invention provides a method for providing a source of oligosaccharides to a human consuming a low-FODMAP diet without inducing gastrointestinal symptoms in the human, the method comprising administering to the human one or more human milk oligosaccharides.

A sixth aspect of the invention is a method of increasing the abundance of bifidobacteria in the colon of a human consuming a low-FODMAP diet, the method comprising administering to the human one or more human milk oligosaccharides. The HMOs preferably increase the abundance and/or relative abundance of bifidobacteria of the *B. adolescentis* phylogenetic group, *Bifidobacterium longum* and/or *Bifidobacterium bifidum*.

Preferably, the human is administered the one or more human milk oligosaccharides for a period of at least 1 week, more preferably for at least 2 weeks. For example, the human can be administered the one or more human milk oligosaccharides for a period of at least 4 weeks.

Preferably, the human is administered an amount of 0.5 g to 15 g per day of the one or more human milk oligosaccharides, more preferably 1 g to 10 g per day. For example, the human may be administered 2 g to 7.5 g per day.

The human may be administered a higher dose initially followed by a lower dose. The higher dose is preferably about 3 g to about 10 g per day (for example about 4 g to about 7.5 g per day) and the lower dose is preferably about 2 g to about 7.5 g per day (for example about 2 g to about 5 g per day).

A seventh aspect of the invention is a method for reintroducing a source of FODMAPs into the diet of a human consuming a low-FODMAP diet, the method comprising (i) administering to the human one or more human milk oligosaccharides prior to the reintroduction of the source of FODMAPs, and (ii) administering to the human one or more human milk oligosaccharides during the reintroduction of FODMAPs.

An eighth aspect of the invention is a method for the secondary prevention of gastrointestinal symptoms in a human reintroducing a source of FODMAPs into a low-FODMAP diet, the method comprising (i) administering to the human one or more human milk oligosaccharides prior to the reintroduction of the source of FODMAPs, and (ii) administering to the human one or more human milk oligosaccharides during the reintroduction of FODMAPs.

A ninth aspect of the invention is a method for prolonging the gastrointestinal benefits of a low-FODMAP diet in a human reintroducing a source of FODMAPs into the human's diet, the method comprising administering to the human one or more human milk oligosaccharides prior to the reintroduction of the source of FODMAPs. Preferably, the human is additionally administered one or more human milk oligosaccharides during the reintroduction of the source of FODMAPs.

In the seventh to ninth aspects, the human is preferably administered the one or more human milk oligosaccharides for a period of at least 1 week, more preferably for at least 2 weeks, prior to the reintroduction of the source of FOD-MAPs. During reintroduction of the source of FODMAPs, the human is preferably administered the one or more human milk oligosaccharides for a period of at least 1 week, more preferably for at least 2 weeks, for example at least 4 weeks.

The human may be administered a higher dose prior to the reintroduction of the source of FODMAPs and a lower dose after reintroduction of the source of FODMAPs. The higher dose is preferably about 3 g to about 10 g per day (for example about 4 g to about 7.5 g per day) and the lower dose is preferably about 2 g to about 7.5 g per day (for example about 2 g to about 5 g per day).

The human may be administered a bifidobacteria in addition to the one or more human milk oligosaccharides. The bifidobacteria may be, for example, *Bifidobacterium longum*, *Bifidobacterium infantis* and/or *Bifidobacterium bifidum*.

The human can be an IBS patient or a non-coeliac wheat and/or gluten sensitivity patient.

DETAILED DESCRIPTION OF THE INVENTION

It has now been surprisingly found that oral or enteral administration of one or more human milk oligosaccharides (HMOs) to a human consuming a low-FODMAP diet permits the human to increase the oligosaccharide content of the diet without inducing significant gastrointestinal symptoms. This allows the human to address some of the nutritional deficiencies of the low-FODMAP diet. Further it allows the human to increase the abundance of bifidobacteria in the colon of the human without inducing significant gastrointestinal symptoms. Usually humans consuming a low FODMAP diet have reduced bifidobacteria abundance and this may have long-term health consequences. The low FODMAP diet requires the reduction or elimination of oligosaccharides from the diet and therefore it is surprising that HMOs may be administered to a human on a low FODMAP diet without inducing significant gastrointestinal symptoms.

It has also been surprisingly found that oral or enteral administration of one or more HMOs to a human consuming a low-FODMAP diet permits the human to reintroduce FODMAPs into his or her diet. Hence the HMOs reduce or prevent reoccurrence gastrointestinal symptoms once sources of FODMAPs are reintroduced into the diet. Ordinarily, reintroduction of FODMAPs leads to resumption of the symptoms. This is problematic because the FODMAPs should be selectively reintroduced to avoid nutritional complications in the long term.

In this specification, the following terms have the following meanings:

"Bifidobacterium of the *B. adolescentis* phylogenetic group" means a bacterium selected from the group consisting of *Bifidobacterium adolescentis*, *Bifidobacterium angulatum*, *Bifidobacterium catenulatum*, *Bifidobacterium pseudocatenulatum*, *Bifidobacterium kashiwanohense*, *Bifidobacterium dentum* and *Bifidobacterium stercoris* (Duranti et al. *Appl. Environ. Microbiol.* 79, 336 (2013), Bottacini et al. *Microbial Cell Fact.* 13:54 (2014)). Preferably, a Bifidobacterium of the *B. adolescentis* phylogenetic group is *Bifidobacterium adolescentis* and/or *Bifidobacterium pseudocatenulatum*.

"Dietary management" means exclusive or partial feeding of patients who, because of a disease, disorder or medical condition are suffering from:
either have a limited, impaired or disturbed capacity to take, digest, absorb, metabolise or excrete ordinary food or certain nutrients contained therein, or metabolites, or
have other medically-determined nutrient requirements (see: Commission Notice on the classification of Food for Special Medical Purposes of the European Commission, *Official Journal of the European Union* C 401, 25.11.2017, p. 10-11).

"Enteral administration" means any conventional form for delivery of a composition to a human that causes the deposition of the composition in the gastrointestinal tract (including the stomach). Methods of enteral administration include feeding through a naso-gastric tube or jejunum tube, oral, sublingual and rectal.

"Effective amount" means an amount of a composition that provides an HMO in a sufficient amount to render a desired treatment outcome in a human. An effective amount can be administered in one or more doses to achieve the desired treatment outcome.

"FODMAP" means a fermentable oligosaccharide, disaccharide, monosaccharide or polyol. They are short chain carbohydrates that are poorly absorbed in the small intestine and include short chain polymers of fructose (fructans) and galactooligosaccharides (GOS, stachyose, raffinose), disaccharides (lactose), monosaccharides (fructose), and sugar alcohols (polyols), such as sorbitol, mannitol, xylitol and maltitol. Sources of FODMAPs include grains, vegetables, fruit, pulses, milk, and food and beverage sweeteners.

"Gastrointestinal symptoms" means symptoms of gastrointestinal discomfort such as bloating, gas production, pain, sensitivity, and altered bowel movement.

"Human milk oligosaccharide" or "HMO" means a complex carbohydrate found in human breast milk (Urashima et al.: *Milk Oligosaccharides*. Nova Science Publisher (2011); Chen Adv. Carbohydr. Chem. Biochem. 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-fucopentaose VI (LNFP-VI), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (FpLNnH II) and fucosyl-lacto-N-neohexaose (FLNnH).

Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Irritable bowel syndrome" and "IBS" mean a group of functional bowel disorders of humans, particularly adults, characterised by one or more chronic symptoms including abdominal pain, abdominal discomfort, abdominal bloating, fatigue, and changes in bowel movement patterns, such as patterns of loose or more frequent bowel movements, diarrhoea and constipation, typically in the absence of any apparent structural abnormality. There are at least three forms of IBS, depending on which symptom predominates: (1) diarrhoea-predominant (IBS-D), (2) constipation-predominant (IBS-C), and (3) IBS with alternating stool pattern (IBS-M). There are also various clinical subtypes of IBS, such as post-infectious IBS (IBS-PI).

"Microbiota", "microflora" and "microbiome" mean a community of living microorganisms that typically inhabits a bodily organ or part, particularly the gastro-intestinal organs of humans. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota, at genus level *Bacteroides, Faecalibacterium, Bifidobacterium, Roseburia, Alistipes, Collinsella, Blautia, Coprococcus, Ruminococcus, Eubacterium* and *Dorea*, at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucous layer covering the epithelium of the gastrointestinal tract, and luminal-associated microbiota, which is found in the lumen of the gastrointestinal tract.

"Modulating of microbiota" means exerting a modifying or controlling influence on microbiota, for example an influence leading to an increase in the indigenous intestinal abundance of *Bifidobacterium, Barnesiella, Faecalibacterium* and/or butyrate producing bacteria. In another example, the influence may lead to a reduction of the intestinal abundance of *Ruminococcus gnavus* and/or Proteobacteria. "Proteobacteria" are a phylum of Gram-negative bacteria and include a wide variety of pathogenic bacteria, such as *Escherichia, Salmonella, Vibrio, Helicobacter, Yersinia* and many other notable genera.

"Non-coeliac wheat sensitivity" means is a syndrome characterised by intestinal and extra-intestinal symptoms related to the ingestion of gluten-containing food, in subjects that are not affected by either coeliac disease or wheat allergy. "Non-coeliac gluten sensitivity" has the same meaning and the two terms are used interchangeably. The gluten-containing food usually contains a gluten-containing cereal such as wheat, barley and rye.

"Non-infant human" or "non-infant" means a human of 3 years of age and older. A non-infant human can be a child, a teenager, an adult or an elderly person.

"Oral administration" means any conventional form for the delivery of a composition to a human through the mouth. Accordingly, oral administration is a form of enteral administration.

"Preventive treatment" or "prevention" means treatment given or action taken to diminish the risk of onset or recurrence of a disease.

"Relative abundance of a bacteria" means the abundance of that bacteria relative to other bacteria in the microbiota of the gastrointestinal tract of a human.

"Relative growth of a bacteria" means the growth of a bacteria relative to other bacteria in the microbiota in the gastrointestinal tract of humans.

"Secondary prevention" means prevention of onset of the condition in a high-risk patient, or prevention of reoccurrence of symptoms in a patient who has already has the condition. A "high-risk" patient is an individual who is predisposed to developing the condition, for example, a person with a family history of the condition "Synthetic composition" means a composition which is artificially prepared and preferably means a composition containing at least one compound that is produced ex vivo chemically and/or biologically, e.g. by means of chemical reaction, enzymatic reaction or recombinantly. In some embodiments, a synthetic composition of the invention is not identical with a naturally occurring composition. The synthetic composition typically comprises one or more HMOs. Also, in some embodiments, the synthetic compositions may comprise one or more nutritionally or pharmaceutically active components which do not affect adversely the efficacy of the HMOs. Some non-limiting embodiments of a synthetic composition of the invention are described below.

"Therapy" means treatment given or action taken to reduce or eliminate symptoms of a disease or pathological condition.

"Treat" means to address a medical condition or disease with the objective of improving or stabilising an outcome in the person being treated or addressing an underlying nutritional need. Treat therefore includes the dietary or nutritional management of the medical condition or disease by addressing nutritional needs of the person being treated. "Treating" and "treatment" have grammatically corresponding meanings.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. Biotechnological methods which describe how to make core (non-fucosylated neutral) human milk oligosaccharides optionally substituted by fucose or sialic acid using genetically modified *E. coli* con be found in WO 01/04341 and WO 2007/101862.

The HMO may be a single HMO or a mixture of any HMOs suitable for the purpose of the invention. In one embodiment, the HMO comprises, consists of or consists essentially of a neutral HMO, preferably a fucosylated neutral HMO, more preferably a fucosylated lactose selected from the group consisting of 2'-FL, 3-FL and DFL, particularly 2'-FL. In other embodiment, the mixture comprises neutral HMOs, preferably at least a first neutral HMO and at least a second neutral HMO. The first neutral HMO is a fucosylated neutral HMO and the second neutral HMO is a core HMO (also referred to as non-fucosylated neutral HMO). Particularly, the mixture of HMOs may contain a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a core HMO selected from the list consisting of LNT, LNnT, LNH, LNnH, pLNH and pLNnH. More preferably, the mixture of neutral HMOs contains, consists of or consists essentially of, a fucosylated HMO selected from the list consisting of 2'-FL, 3-FL and DFL, and a core HMO selected from the list consisting of LNT and LNnT, advantageously the mixture comprises, consists of or consists essentially of, 2'-FL and at least one of LNnT and LNT, or at least one of 2'-FL and DFL and at least one of LNnT and LNT, or 2'-FL, DFL and at least one of LNnT and LNT.

In a mixture comprising, consisting of or consisting essentially of, 2'-FL and at least one of LNnT and LNT, the mixture contains more 2'-FL than LNnT and/or LNT. Preferably, the mass ratio of 2'-FL to LNnT and/or LNT in the mixture is about 1.5 to about 4.5. In one embodiment, the mass ratio of 2'-FL to LNnT and/or LNT in the mixture is about 1.5 to about 2.5, for example about 2:1. In another embodiment, the mass ratio of 2'-FL to LNnT and/or LNT in the mixture is about 3.5 to about 4.5, for example about 4:1.

In other embodiment, the mixture comprises at least a first (acidic) HMO and at least a second (neutral) HMO, wherein the first (acidic) HMO is selected from the list consisting of 3'-SL, 6'-SL and FSL and the second (neutral) HMO is selected from the list consisting of 2'-FL, 3-FL, DFL, LNT and LNnT. Advantageously, the mixture comprises 2'-FL and 6'-SL, or 6'-SL and at least one of 2'-FL and DFL, or 2'-FL, 6'-SL and at least one of LNnT and LNT, or 2'-FL, DFL, 6'-SL and at least one of LNnT and LNT.

The HMO or HMOs can be used as it is or they are (neat), without any carrier and/or diluent. In other embodiment, the HMO/HMOs is/are used in a synthetic composition with one or more inert carriers/diluents that are acceptable in nutritional or pharmaceutical compositions, for example solvents (e.g. water, water/ethanol, oil, water/oil), dispersants, coatings, absorption promoting agents, controlled release agents, inert excipients (e.g. starches, polyols, granulating agents, microcrystalline cellulose, diluents, lubricants, binders, disintegrating agents). These compositions do not contain prebiotic and/or probiotic. In other embodiment, the HMO/HMOs is/are used in a synthetic pharmaceutical or nutritional composition that may contain a prebiotic and/or probiotic.

The synthetic composition can be in the form of a nutritional composition. For example, the nutritional composition can be a food composition, a rehydration solution, a medical food or food for special medical purposes, a nutritional supplement and the like. The nutritional composition can contain sources of protein, lipids and/or digestible carbohydrates and can be in powdered or liquid forms. The composition can be designed to be the sole source of nutrition or as a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for humans with inflamed or compromised GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the gastrointestinal tract and can improve intestinal barrier function and mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g. maltitol, erythritol, sorbitol), or mixtures thereof. Preferably, the composition is reduced in or free from added lactose or other FODMAP carbohydrates. Generally digestible carbohydrates provide about 35% to about 55% of the energy of the nutritional composition. A particularly suitable digestible carbohydrate is a low dextrose equivalent (DE) maltodextrin.

Suitable lipids include medium chain triglycerides (MCT) and long chain triglycerides (LCT). Preferably, the lipid is a mixture of MCTs and LCTs. For example, MCTs can comprise about 30% to about 70% by weight of the lipids, more specifically about 50% to about 60% by weight. MCTs offer the advantage of easier digestion which can be important for humans with inflamed or compromised GI tracts. Generally, the lipids provide about 35% to about 50% of the energy of the nutritional composition. The lipids can contain essential fatty acids (omega-3 and omega-6 fatty acids). Preferably, these polyunsaturated fatty acids provide less than about 30% of total energy of the lipid source.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition may also include vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 μg/ml to about 10 μg/ml. Lutein can be included in an amount of from about 0.001 μg/ml to about 10 μg/ml, preferably from about 0.044 μg/ml to about 5 μg/ml of lutein. Lycopene can be included in an amount from about 0.001 μg/ml to about 10 μg/ml, preferably about 0.0185 μg/ml to about 5 μg/ml of lycopene. Beta-carotene can comprise from about 0.001 μg/ml to about 10 mg/ml, for example about 0.034 μg/ml to about 5 μg/ml of beta-carotene.

The nutritional composition preferably also contains reduced concentrations of sodium, for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l, and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. lactis BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be formulated as a soluble powder, a liquid concentrate, or a ready-to-use formulation. The composition can be fed to a human in need via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, it may be preferred that the total concentration of HMOs in the liquid, by weight of the liquid, is from about 0.1% to about 1.5%, including from about 0.2% to about 1.0%, for example from about 0.3% to about 0.7%. When the nutritional product is a concentrated nutritional liquid, it may be preferred that the total concentration of HMOs in the liquid, by weight of the liquid, is from about 0.2% to about 3.0%, including from about 0.4% to about 2.0%, for example from about 0.6% to about 1.5%.

In another embodiment, the nutritional composition is in a unit dosage form. The unit dosage form can contain an acceptable food-grade carrier, e.g. phosphate buffered saline solution, mixtures of ethanol in water, water and emulsions such as an oil/water or water/oil emulsion, as well as various wetting agents or excipients. The unit dosage form can also contain other materials that do not produce an adverse, allergic or otherwise unwanted reaction when administered to a human. The carriers and other materials can include solvents, dispersants, coatings, absorption promoting agents, controlled release agents, and one or more inert excipients, such as starches, granulating agents, microcrystalline cellulose, diluents, lubricants, binders, and disintegrating agents. Preferably, carriers and other materials are low in FODMAPs or contain no FODMAPs. Preferably, the unit dosage form comprises primarily HMOs with a minimum amount of binders and/or excipients. Unit dosage forms are particularly suitable when nutritionally incomplete or not intended as a sole source of nutrition.

A unit dosage form of this invention can be administered orally, e.g. as a tablet, capsule, or pellet containing a predetermined amount of the mixture, or as a powder or granules containing a predetermined concentration of the mixture or a gel, paste, solution, suspension, emulsion, syrup, bolus, electuary, or slurry, in an aqueous or non-aqueous liquid, containing a predetermined concentration of the mixture. An orally administered composition can include one or more binders, lubricants, inert diluents, flavouring agents, and humectants. An orally administered composition such as a tablet can optionally be coated and can be formulated to provide sustained, delayed or controlled release of the HMO.

A unit dosage form of this invention can also be administered by naso-gastric tube or direct infusion into the GI tract or stomach.

A unit dosage form of this invention can also include therapeutic agents such as antibiotics, probiotics, analgesics, and anti-inflammatory agents. The proper dosage of such a composition for a human can be determined in a conventional manner, based upon factors such as the human's condition, immune status, body weight and age. In some cases, the dosage will be at a concentration similar to that found for the HMOs of the composition in human breast milk. The required amount would generally be in the range from about 0.5 g to about 15 g per day, in certain embodiments from about 1 g to about 10 g per day, for example about 2 g to about 7.5 g per day. Appropriate dose regimes can be determined by methods known to those skilled in the art.

In further embodiment, the HMO can be formulated as a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to humans. The carriers and other materials can include solvents, dispersants, coatings, absorption promoting agents, controlled release agents, and one or more inert excipients, such as starches, granulating agents, microcrystalline cellulose, diluents, lubricants, binders, and disintegrating agents. Preferably, carriers and other materials are low in FODMAPs or contain no FODMAPs.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antibiotics, probiotics, analgesics, and anti-inflammatory agents. The proper dosage of these compositions for a human can be determined in a conventional manner, based upon factors such condition, immune status, body weight and age. In some cases, the dosage will be at a concentration similar to that found for the HMOs in human breast milk. The required amount would generally be in the range from about 0.5 g to about 15 g per day, in certain embodiments from about 1 g to about 10 g per day, for example from about 2 g to about 7.5 g per day. Appropriate dose regimes can be determined by conventional methods.

The amount of HMOs required to be administered for (i) providing a source of oligosaccharides to a human consuming a low-FODMAP diet, (ii) increasing the abundance of bifidobacteria in the colon of a human consuming a low-FODMAP diet, (iii) reintroducing FODMAPs into the diet of a human consuming a low-FODMAP diet, and/or (iv) prolonging gastrointestinal symptom reduction in a human tapering off or terminating a low-FODMAP diet, will vary depending upon factors such as the risk and severity of the underlying condition requiring the use of a low-FODMAP diet, any other medical conditions or diseases, age, the form of the composition, and other medications being administered. Further the amount may vary depending upon whether the HMOs are being used to deliver a direct effect (when the dose may be higher) or whether the HMOs are being used as a secondary prevention/maintenance (when the dose may be lower). However, the required amount can be readily set by a medical practitioner and would generally be in the range from about 0.5 g to about 15 g per day, in certain embodiments from about 1 g to about 10 g per day, for example from about 2 g to about 7.5 g per day. An appropriate dose can be determined based on several factors, including, for example, body weight and/or condition, the severity of the underlying condition being treated or prevented, other ailments and/or diseases, the incidence and/or severity of side effects and the manner of administration. Appropriate dose ranges may be determined by methods known to those skilled in the art. During an initial treatment phase, the dosing can be higher (for example 3 g to 15 g per day, preferably 4 g to 7.5 g per day). During a maintenance phase, the dosing can be reduced (for example, 1 g to 10 g per day, preferably 2 g to 7.5 g per day, more preferably about 2 g to about 5 g per day)).

EXAMPLES

Examples are now described to further illustrate the invention:

Example 1—Human Trial

A total of 60 male and female IBS patients are recruited to participate in the study. After a screening visit and run-in period of 1-2 weeks, the patients are selected. The patients are randomised into two groups, each of 30 patients, with one group consuming the treatment product and one group the placebo product. The treatment product contains 5 grams of a combination of 2'-FL and LNnT in a 4:1 ratio, while the placebo product contains 5 grams glucose. Both products are in powder form in a unit dosage container.

The patients are eligible to participate if they are at an age between 18-60 years, fulfil definition of IBS-D, IBS-C or IBS-M according to the Rome IV criteria for IBS and have a global IBS-SSS score of >174 during the 2 weeks run-in period. All recruited patients are able and willing to understand and comply with the study procedures. Patients are excluded if: they have any known gastrointestinal disease(s) that may cause symptoms or interfere with the trial outcome, in particular lactose intolerance and coeliac disease, they have participated in a clinical study one month prior to screening visit, they have abnormal results in the screening tests which are clinically relevant for study participation, they are suffering for a severe disease such as malignancy, diabetes, severe coronary disease, kidney disease, neurological disease, or severe psychiatric disease or any condition which can confound the results of the study, they have used highly dosed probiotic supplements (yoghurt allowed) for 1 months prior to the study, they have consumed antibiotic drugs 1 months prior to the study, they have consumed on a regular basis any medication that might interfere with symptom evaluation 2 weeks prior to the study, they have been diagnosed with and treated for IBS for more than 10 years; and they are pregnant or lactating.

At the screening visit (visit 1), clinical and medical history and concomitant medication is registered. IBS diagnostic criteria will be assessed and part 2 of the IBS-SSS questionnaire is completed.

A faecal sample kit is distributed together with a Bristol Stool Form Scale (BSFS) and Bowel Movement Diary (BMD) which is to be filled in during the 7 days just prior to the second visit. Patients are asked to register their diet 3 days just prior to visit 2 and are reminded not to change their usual diet during the study.

At the second visit (visit 2), eligibility criteria are checked, and eligible subjects are randomised to the two arms in the trial. A physical examination is done and several questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Based on clinical symptoms and data from questionnaires, patients are characterised into one of the three following groups: diarrhoea predominant (IBS-D), constipation predominant (IBS-C) or mixed (IBS-M). This enables allocation of patients from each subgroup into the intervention groups. Patients are asked about any adverse events and any changes in their usual medication. The BSFS and BMD are collected and new forms, to be filled in daily during the intervention period, are distributed. Faecal samples are collected and equipment for new samples are distributed. Blood samples are collected for routine clinical chemistry and haematology and biomarker analysis and a saliva sample is collected to analyse FUT2 secretor status. Diet records are collected, and new forms are distributed. The randomised patients are then given a 4-week supply of the placebo product or the treatment product depending upon the group they are randomised to. The patients and clinical staff are blinded to which product is received. Patients are instructed to consume the intervention products in the morning with breakfast. The randomised patients are then counselled by a trained research dietitian on the low FODMAP diet. The diet records are used to monitor compliance with the low FODMAP diet.

At the third visit (visit 3) after 4 weeks, a physical examination is performed and a number of questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Food and compliance diaries are collected to check compliance. Blood samples are collected for routine clinical chemistry and haematology and biomarker analysis. Patients are asked about any adverse events and any changes in their usual medication. Faecal samples are collected and equipment for collecting new samples distributed. The BSFS and BMD is collected and new forms, to be filled in during the 7 days just prior to visit 4, are distributed. Diet records are collected, and new forms are distributed. The patients are then counselled by a trained research dietitian on discontinuation of the FODMAP diet.

At the fourth visit (visit 4) two weeks after visit 3, each patient has an exit visit with the medical team. Faecal samples and blood samples are collected and analysed as before. A number of questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Patients are asked about any adverse events and any changes in their usual medication or diet, and the BSFS and BMD are collected To assess the microbiota profile, DNA is extracted from faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al. *Nucleic Acids Res.* 41, e1 (2013)). These are universal bacterial 16S rDNA primers, which target the V3-V4 region. Following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH is used for bioinformatical analysis of the sequence data.

Between Visit 2 and Visit 3, all patients tolerate the low FODMAP diet with no difference in tolerance between the groups. All patients improve gastrointestinal symptoms. Patients receiving the treatment product have elevated bifidobacteria levels as compared to the placebo group at Visit 3. At visit 4, patients who received the treatment product between Visits 2 and 3 continue to show improved gastrointestinal symptoms. The patients who received the placebo product between Visits 2 and 3 show worsened gastrointestinal symptoms.

At Visit 4, all patients are invited to participate in an open label extension of the trial. Patients agreeing to participate are provided with 48 days of the treatment product. After 48 days, the patients complete the GSRS-IBS and IBS-SSS questionnaires on a web-based, data collection system.

Patients who consumed the treatment product between Visits 2 and 3 show no worsening of gastrointestinal symptoms despite the reintroduction of sources of FODMAPs into their diet.

Example 2—Nutritional Product

A ready to feed nutritional composition is prepared from water, milk protein concentrate, maltodextrin, sugar, milk protein concentrate, canola oil, soy protein isolate, caseinate, HMO (2'-FL), cellulose gel and gum, flavours, soy lecithin, carrageenan gum, and vitamins and mineral. The product is aseptically filled into 200 ml bottles and seal.

The composition provides a nutritional supplement which is a good source of protein, oligosaccharides in the form of 2'-FL, vitamins, minerals and antioxidants, is low in fat, and meets FODMAP criteria.

Example 3—Human Trial

Interested healthy individuals are recruited for the study. The individuals are screened to determine if they are between the ages of 18 and 65, have a BMI between 18.5 and 30 kg/m$^2$, and can provide written, informed consent. Individuals are excluded based on use of enemas, laxatives, proton pump inhibitors, or antibiotics within the past 3 months, history of past or current gastrointestinal conditions, high fibre consumption, and regularly skipping breakfast and/or lunch. Individuals with known allergies to any ingredients in the treatments, or recent participation in another dietary intervention trial are also excluded. A total of 20 healthy adults meeting all of the inclusion and exclusion criteria are enrolled in the study. Informed consent was obtained from each participant before the commencement of the study.

The participants are asked to follow a low-fibre diet and avoid sugar alcohols and other sources of FODMAPs for 24 hours before the treatment visit. Also, the participants are required to undergo an overnight fast prior to the treatment visit. At the treatment visit, the individuals asked to consume 200 ml of either a positive control or a treatment product.

The positive control is a lactose-free milk containing 5 g of fructooligosaccharides. The treatment product is the product of example 2. The participants are asked to fill out a GSRS questionnaire to determine gastrointestinal symptoms.

Breath hydrogen is measured at baseline, and then at 1, 2, 3, and 4 h after consumption of the positive control or treatment product. This is done by instructing participants to breathe into a breath collection bag, and 20 ml of the end expiratory air was removed and tested. The samples are analysed using the Quintron GaSampler System for hydrogen and methane content. The GSRS is completed at baseline, and then at 1, 2, 3, and 4 hours following consumption of the intervention product.

Both intervention products are well tolerated in the healthy participants. The treatment product produced a lower breath hydrogen response compared to the positive control.

Example 4—Capsule Composition

A capsule is prepared by filling about 1 g of HMO into a 000 gelatine capsule using a filing machine. The capsules are then closed. The HMO are in free flowing, powder form.

Example 5—Nutritional Composition

The HMOs 2'-FL and LNnT are introduced into a rotary blender in a 4:1 mass ratio. An amount of 0.25 w % of silicon dioxide is introduced into the blender and the mixture blended for 10 minutes. The mixture is then agglomerated in a fluidised bed and filled into 5 gram stick packs and the packs are sealed.

The invention claimed is:

1. A method comprising:
providing to a non-infant human consuming a low-FODMAP diet for reducing gastrointestinal symptoms incident to a diagnosis of irritable bowel syndrome (IBS) made after excluding confounding conditions comprising lactose intolerance and celiac disease, a composition comprising a dosage of one or more neutral human milk oligosaccharides (HMOs), the composition formulated for permitting subsequent or concurrent reintroduction of FODMAPs into a diet without inducing gastrointestinal symptoms in the non-infant human and increasing a relative abundance of adult-type bifidobacteria endogenous to the colon of the non-infant human, wherein the reintroduced FODMAPs contain one or more of: fructans, galactooligosaccharides (GOS), fructose, and/or polyols; and
providing instructions to reintroduce a suitable source of the FODMAPs into the diet of the non-infant human after or during consumption of the composition comprising the dosage of the one or more neutral HMOs during an initial phase, wherein the suitable source of the FODMAPS is reintroduced into the diet of the non-infant human without an increase in levels of the one or more gastrointestinal symptoms relative to levels prior to beginning the initial phase.

2. The method of claim 1, wherein the source of the FODMAPs is reintroduced into the diet of the non-infant human during a maintenance phase without increasing the levels of the one or more gastrointestinal symptoms in the non-infant human relative to the levels of the one or more gastrointestinal symptoms prior to the initial phase.

3. The method of claim 1, wherein the one or more gastrointestinal symptoms are selected from the group consisting of satiety, abdominal pain, diarrhoea, constipation, bloating, and combinations thereof.

4. The method of claim 1, wherein increasing the relative abundance of the adult-type bifidobacteria in the colon of a non-infant human comprises increasing the relative abundance of *Bifidobacterium adolescentis*.

5. The method of claim 1, wherein increasing the relative abundance of the adult-type bifidobacteria in the colon of a non-infant human comprises increasing the relative abundance of *Bifidobacterium longum* subsp. *longum* (*B. longum*).

6. The method of claim 1, wherein increasing the relative abundance of the adult-type bifidobacteria in the colon of a non-infant human comprises increasing the relative abundance of *Bifidobacterium bifidum*.

7. The method of claim 1, wherein the one or more neutral HMOs are selected from the group consisting of 2'-Fucosyllactose (2'-FL), 3-Fucosyllactose (3-FL), Difucosyllactose (DFL), Lacto-N-fucopentaose I (LNFP-I), Lacto-N-tetraose (LNT), Lacto-N-neotetraose (LNnT), and combinations thereof.

8. The method of claim 7, wherein the one or more neutral HMOs comprise a mixture of:
one or more fucosylated HMOs selected from the group consisting of 2'-FL, 3-FL, DFL, LNFP-I, and combinations thereof; and
one or more non-fucosylated HMOs selected from the group consisting of LNT, LNnT, and combinations thereof.

9. The method of claim 8, wherein the mixture consists of:
one or more fucosylated HMOs selected from the group consisting of 2'-FL, 3-FL, DFL, LNFP-I, and combinations thereof;
one or more non-fucosylated HMOs selected from the group consisting of LNT, LNnT, and combinations thereof; and
one or more excipients.

10. The method of claim 1, wherein the initial phase comprises a period of at least 1 week.

11. The method of claim 1, wherein the dosage during the initial phase comprises an amount of 3 g to 10 g per day of the one or more neutral HMOs.

12. The method of claim 1, further comprising instructing the non-infant human to reduce the dosage of the one or more neutral HMOs after the reintroduction of FODMAPs during a maintenance phase, wherein the suitable source of the FODMAPs is reintroduced into the diet during the maintenance phase without an increase in the gastrointestinal symptoms.

13. The method of claim 12, wherein the dosage during the maintenance phase comprises an amount of 2 g to 7.5 g per day of the one or more neutral HMOs.

* * * * *